US006572855B1

United States Patent
Johnsson et al.

(10) Patent No.: US 6,572,855 B1
(45) Date of Patent: *Jun. 3, 2003

(54) USE OF HYALURONIDASE IN THE MANUFACTURING OF A DRUG FOR THE TREATMENT OF INFLAMMATION

(75) Inventors: Cecilia Johnsson, Uppsala (SE); Gunnar Tufveson, Uppsala (SE); Roger Hällgren, Bälinge (SE); Bengt Gerdin, Uppsala (SE)

(73) Assignee: Linc Invest AB, Brottby (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/462,362
(22) PCT Filed: May 6, 1998
(86) PCT No.: PCT/SE98/00831
§ 371 (c)(1),
(2), (4) Date: Jan. 7, 2000
(87) PCT Pub. No.: WO99/02181
PCT Pub. Date: Jan. 21, 1999

(30) Foreign Application Priority Data

Jul. 9, 1997 (SE) ................................. 9702657

(51) Int. Cl.$^7$ ........................... A61K 38/46; C12N 9/26
(52) U.S. Cl. ..................................... 424/94.62; 435/201
(58) Field of Search ...................... 424/94.62; 435/201

(56) References Cited

U.S. PATENT DOCUMENTS 5,747,027 A * 5/1998 Stern et al. .............. 424/94.62

FOREIGN PATENT DOCUMENTS

| EP | 0193330 | 9/1986 |
| SE | 509350 | 1/1999 |
| WO | 9631596 | 10/1996 |
| WO | 9800553 | 1/1998 |

OTHER PUBLICATIONS

"The Merck Index", 1996, 12th edition, p. 814.*
"Physician's Desk Reference", 1997, 51st. edition, p. 2930.*
Taira et al., Angiology–The Journal of Vascular Diseases, 1029–1035, Dec. 1990.*
Grossman et al., Annals of Plastic Surgery, vol. 11, No. 3, 223–226, 1983.*
Fischer et al., Transplant. Int., 9 (Suppl. 1), S442–S446, 1996.*
Laurent et al., "Nomenclature of Hyaluronic acid", *Biochemical Journal*, vol. 235, pp. 903, (1986).
Comper et al., "Physiological Function of Connective Tissue Polysaccharides", *Physiological Review*, vol. 58 No. 1, pp. 255–315, (1978).

Nettelbladt et al., "Accumulation of Hyaluronic Acid in Alveolar Interstitial Tissue in Bleomycin–induced Alveolitis", *Am. Rev. Respir.*, vol. 139, pp. 759–762, (1989).

Waldenstrom et al., "Accumulation of Hyaluronan and Tissue Edema in Experimental Myocardial Infarction" *J. Clin. Invest.*, vol. 88, pp. 1622–1628, (1991).

Hallgren et al., "Hyaluronic Acid Accumlation and Redistribution in Rejecting Rat Kidney Graft", *J. Exp. Med* vol. 171, pp. 2063–2076, (1990).

Wells et al., "The Localization Hyaluronan in Normal and Refected Human Kidneys", *Transplantion*, vol. 50 No. 2, pp. 240–243, (1990).

Wallander et al., "Intestinal distrubution of hyaluronan in small bowell allografting in the rat" *Transplant International*, vol. 6, 133–137, (1993).

Hallgren et al., "Accumulation of Hyaluronan (Hyaluronic Acid) in Myocardial Interstitial Tissue Paralles Development of Transplantation Edema in Heart Allografts in Rats", *J. Clin. Invest.*, vol. 85, No. 3, pp. 667–673, (1990).

Waldenstrom et al., "Coxsackie B3 myocarditis induced a decrease in energy charge and accumulation of hyaluronan in the mouse heart", *Euro. J. Clin. Invest.*, vol. 23, pp. 277–282, (1993).

Mason, "Recent Advances in the Biochemistry of Hyaluronic Acid in Cartilage", *Chemistry, Biology, and Physiology*, pp. 87–112, (1981).

Maroko et al, "Reduction by Hyaluronidase of Myocardial Necrosis following Coronary Artery Occlusion" *Circulation*, vol. 1006, pp. 430–437, (1972).

Rovetto, "Effect of Hyaluronidase and Methylprednisolone on Myocardial Function, Glucose Metabolism, and Coronary Flow in the Isolated Ischemic Rat Heart", *Circulation Research*, vol. 41, No. 3, pp. 372–379, (1977).

Fischer et al., "Adding a New Principle to Hypothermic Storage Preservatin–Reduction of Edema Formation by Hyaluronidase", *Transplantation*, vol. 58, No. 6, (1994).

* cited by examiner

Primary Examiner—Michael V. Meller
(74) Attorney, Agent, or Firm—Browdy and Neimark PLLC

(57) ABSTRACT

Hyaluronidase is used in the treatment of inflammation associated with an increased local synthesis of hyaluronan in a mammal, e.g. in connection with organ grafting, hyaluronidase being administered locally or systemically. The effect is to reduce inflammatory cell infiltration.

7 Claims, No Drawings

USE OF HYALURONIDASE IN THE MANUFACTURING OF A DRUG FOR THE TREATMENT OF INFLAMMATION

CROSS REFERENCE TO RELATED APPLICATION

The present application is the national stage under 35 U.S.C. 371 of PCT/SE98/00831, filed May 6, 1998.

The present invention relates to the use of hyaluronidase in the manufacturing of a pharmaceutical for the treatment of a mammal suffering from inflammation associated with an increased local synthesis of hyaluronan. More specifically it relates to the use of hyaluronidase in the manufacturing of a pharmaceutical for the prevention of inflammatory cell infiltration caused by hyaluronan.

BACKGROUND OF THE INVENTION

Hyaluronidase is an enzyme produced in e.g. mammals, leeches, and krill and which is extractable from a number of tissues. Hyaluronidase degrades a mucopolysaccharide called hyaluronan, also referred to as hyaluronic acid (Balazs E A et al, Biochem J 1986; 235: 903). Hyaluronan is an important stabilizing constituent of the loose connective tissue and is produced by the mesenchymal cells (Comper W D, Laurent T C, Physiol Rev 1978; 58: 255–315).

The content of hyaluronan in an organ has been shown to increase in different conditions of inflammation of that organ. Thus, an increased concentration of hyaluronan has been shown in tissue from different organs characterized by a condition of inflammatory-immunological injury such as alveolitis (Nettelbladt O et al, Am Rev Resp Dis 1989; 139: 759–762) and myocardial infarction (Waldenström et al, J Clin Invest 1991; 88(5): 1622–1628). Other examples of this type of conditions are the allograft rejection after a renal (H ällgren et al, J Exp Med 1990a; 171: 2063–2076; Wells et al, Transplantation 1990; 50: 240–243), small bowel (Wallander et al, Transplant Int 1993; 6: 133–137) or cardiac (Hällgren et al, J Clin Invest 1990b;85:668–673) transplantation; or a myocardial inflammation of viral origin (Waldenström et al, Eur J Clin Invest 1993; 23: 277–282).

Hyaluronan is a compound with a pronounced water binding capacity (Mason R M, Progr Clin Biol 1981; Res 54:87–112). An enhanced local production and accumulation of hyaluronan in the connective tissue of an organ therefore leads to a local accumulation of liquid, with a risk of harmful interstitial tissue edema, which in turn may lead to an impairment of the function of that organ.

It is clear that this accumulation of hyaluronan in e.g. an organ in a state of inflammation may bring about very severe consequences. In the case of an organ transplantation it also may lead to irreversibility of a rejection of the organ and in some cases eventually to a life threatening condition. Therefore it exists a great demand for a method of alleviating this state of risk. The object of the present invention is to provide a means of achieving this.

Hyaluronidase has previously, in the seventies, been used to reduce the effects of myocardial infarction (Maroko P R et al, Circulation 1972; 46(3): 430–7; Maclean D, et al, Science 1976; 194(4261): 199–200). The mode of action was however not understood. In an in vitro animal model cardiac performance after ischemic injury was improved upon administration of hyaluronidase (Rovetto M J, Circ Res 1977; 41(3): 373–9; Fischer J H et al, Transplantation 1994; 58(6): 748–53).

In spite of the fact that for a certain time already it has been known that interstitial edema by a graft rejection could be the result of an interstitial accumulation of hyaluronan, it never has been proposed to make use of hyaluronidase to overcome the very serious clinical problem of allograft rejection due to inflammation.

In fact there existed several reasons for the persons skilled in the art not to believe this would be an operable solution to the problem.

Firstly, it was regarded as most improbable that the enzyme would reach the inflamed tissue.

Secondly, even if the enzyme did reach the inflamed tissue, it was regarded as improbable that it would be functional, since the pH optima of hyaluronidases are quite acidic, whereas the pH in the tissue is neutral.

Finally, it was considered that if the enzyme nonetheless would be active, then this might lead to a degradation of hyaluronan in the whole of the body, and not essentially only in the inflamed tissue.

Thus, although hyaluronidase has been used in laboratory tests on cell cultures and laboratory animals, there has been a general prejudice among the persons skilled in the art against its use on human beings.

Most scientists at present believe the inflammatory cells are recruited to the organs by means of them being on a specific mission to the organ. To our great surprise not only graft edema was diminished by hyaluronidase treatment but also inflammatory cell infiltration was reduced. This means that hyaluronan acts as a magnet for recruitment of inflammatory cells. This may be explained by the fact that lymphocytes carry receptors for hyaluronan. The function of these receptors were previously not understood.

GENERAL DESCRIPTION OF THE INVENTION

The present inventors have been able to show that prophylactic treatment with hyaluronidase delays rejection of a non-immunosuppressed allograft and reduces inflammatory cell infiltrates. This finding means quite unexpectedly that hyaluronan acts as a magnet for inflammatory cells. This mechanism could be universally applied to reduce ongoing inflammation by means of reducing inflammatory recruitment. This to a man skilled in the art very surprising finding led the present inventors to develop a pharmaceutical based on hyaluronidase for the treatment of conditions of inflammation associated with an increased local syntesis of hyaluronan.

The object of the present invention consequently is the use of hyaluronidase in the manufacturing of a pharmaceutical for the treatment of conditions of inflammation associated with an increased local syntesis of hyaluronan.

Another object of the invention is to provide a method of treating conditions of inflammation associated with an increased local synthesis of hyaluronan, by systemic or local treatment with a pharmaceutical comprising hyaluronidase.

The invention will be described in further detail herein below and is defined in the appended claims.

DETAILED DESCRIPTION OF THE INVENTION

One preferred embodiment of the invention refers to the use of hyaluronidase in the manufacturing of a pharmaceutical for the treatment of conditions of inflammation in a mammal of animal or human origin. This treatment may be of a preventive or curative character.

In an especially preferred embodiment, hyaluronidase is used in the manufacturing of a pharmaceutical for the treatment of a condition of inflammation associated with an organ grafting. The organ may e.g. be a liver, a kidney or a heart, of a mammal of animal or human origin.

According to the invention hyaluronidase is used in the manufacturing of a pharmaceutical to be administred systemically or locally.

Hyaluronidase should be incorporated in the pharmaceutical in such an amount as to give a daily dosage of from 1 IU to 20 000 IU by kg of the body weight, more preferably from 100 IU to 15 000 IU by kg of the body weight, or from 500 IU to 10 000 IU by kg of the body weight, by systemic or local administration of the pharmaceutical.

The pharmaceutical of the invention is prepared in a conventional way, known to the person skilled in the art. The locally applied pharmaceutical may in addition to hyaluronidase contain constituents of conventional organ preservation solutions, such as dextran, anions, cations, and osmotic molecules. Its systemic use form may contain stabilizing agents and saline.

The invention also relates to a method of creating a mammal suffering from a condition of inflammation associated with an increased local synthesis of hyaluronan. One preferred embodiment of the invention is a method of treating a mammal suffering from a condition of inflammation associated with increased local synthesis of hyaluronan, by systemic or local treatment with a pharmaceutical comprising hyaluronidase.

One especially preferred embodiment of the invention is a method of treating a mammal suffering from a condition of inflammation occurring in connection with organ grafting and which is associated with increased local synthesis of hyaluronan, by systemic or local treatment with a pharmaceutical comprising hyaluronidase.

In the method of the invention the pharmaceutical is systemically or locally administered to a mammal in an amount giving a daily dosage of from 1 to 80,000 IU of hyaluronidase/kg/body weight of said mammal, more preferably from 100 IU to 20 000 IU by kg of the body weight by local or systemic administration of the pharmaceutical.

The invention has so far been tested in a rat model of male Wistar rats weighing approximately 180 g. The rats were grafted heterotopically with a vascularized cardiac graft. 20 grafts were performed. 10 animals recieved daily injections of hyaluronidase 20 000 IU/kg bw/day iv. The treated group grafts (determined by daily palpation for beat of the graft) survived for 9.7+/−0.5 days and the control group (untreated) animals survived for only 8.3+/−0.3 days (the difference being significant p<0.01). At day six another 21 grafts were examined for inflammatory cell content. They were sequentially ranked for their inflammatory cell content. The rank figure for normality was significantly better in the treated animals (treated with hyaluronidase as above). The experiment thereby shows that cell infiltrates are smaller when hyaluronidase is given. It seems that hyaluronan is at least partially responsible for the recruitement of inflammatory cells which in turn causes graft rejection.

What is claimed is:

1. A method for treating a patient who has received a non-immunosuppressed allograft in order to delay rejection of the allograft and to reduce inflammatory cell infiltrates comprising administering to said patient who has received the allograft and an effective amount of hyaluronidase wherein said patient is suffering from at least one of rejection of the allograft and inflammatory cell infiltration.

2. The method according to claim 1 wherein the allograft is selected from the group consisting of heart, liver, and kidney.

3. The method according to claim 1 wherein the hyaluronidase is administered systemically.

4. The method according to claim 3 wherein the hyaluronidase is administered in conjunction with stabilizing agents and saline.

5. The method according to claim 1 wherein the hyaluronidase is administered locally.

6. The method according to claim 5 wherein the hyaluronidase is combined with a compound for organ preservation.

7. The method according to claim 1 wherein the hyaluronidase is administered prophylactically.

* * * * *